(12) United States Patent
Wehbi

(10) Patent No.: US 11,779,735 B2
(45) Date of Patent: Oct. 10, 2023

(54) HOUSING FOR STORAGE AND MANIPULATION OF A SURGICAL GUIDE WIRE

(71) Applicant: The Regents of the University of California, Oakland, CA (US)

(72) Inventor: Elias Wehbi, Newport Beach, CA (US)

(73) Assignee: The Regents of the University of California, Oakland, CA (US)

( * ) Notice: Subject to any disclaimer, the term of this patent is extended or adjusted under 35 U.S.C. 154(b) by 277 days.

(21) Appl. No.: 16/911,855

(22) Filed: Jun. 25, 2020

(65) Prior Publication Data
US 2021/0008352 A1 Jan. 14, 2021

Related U.S. Application Data

(60) Provisional application No. 62/866,165, filed on Jun. 25, 2019.

(51) Int. Cl.
*A61M 25/09* (2006.01)

(52) U.S. Cl.
CPC .............. *A61M 25/09041* (2013.01); *A61M 2025/09116* (2013.01)

(58) Field of Classification Search
CPC ... A61B 1/0051; A61B 1/0052; A61B 1/0053; A61M 25/0105; A61M 25/0113; A61M 25/0133–0158; A61M 25/09041; A61M 25/0905; A61M 2025/09116; A61M 2025/09125
See application file for complete search history.

(56) References Cited

U.S. PATENT DOCUMENTS

| | | | | |
|---|---|---|---|---|
| 6,533,772 | B1 * | 3/2003 | Sherts | A61M 25/0136 279/42 |
| 2005/0245847 | A1 * | 11/2005 | Schaeffer | A61M 25/09041 600/585 |
| 2018/0333560 | A1 * | 11/2018 | Milner | A61M 25/0136 |
| 2020/0315430 | A1 * | 10/2020 | Ward-Booth | A61B 1/0052 |

* cited by examiner

*Primary Examiner* — David J. McCrosky
(74) *Attorney, Agent, or Firm* — Brooks Kushman P.C.

(57) ABSTRACT

A housing has a spiral passageway for a catheter that is manually extracted from the housing by means of a wheel having a textured circumferential surface and mounted on a shaft that extends through a non-circular bearing defined in an outer portion of the housing. An inner portion of the wheel extends into the spiral passageway adjacent the wire catheter and an outer portion of the wheel outwardly from the housing whereby the upper surface of the knob can be manipulated in one direction and the wire catheter below the knob will be advanced in the opposite direction. The non-circular bearing has a generally circular outer portion in which the textured surface of the knob is only intermittently in contact with the catheter whereby the wire catheter may be advanced, and a generally linear inner portion sloping inwardly towards the catheter.

4 Claims, 4 Drawing Sheets

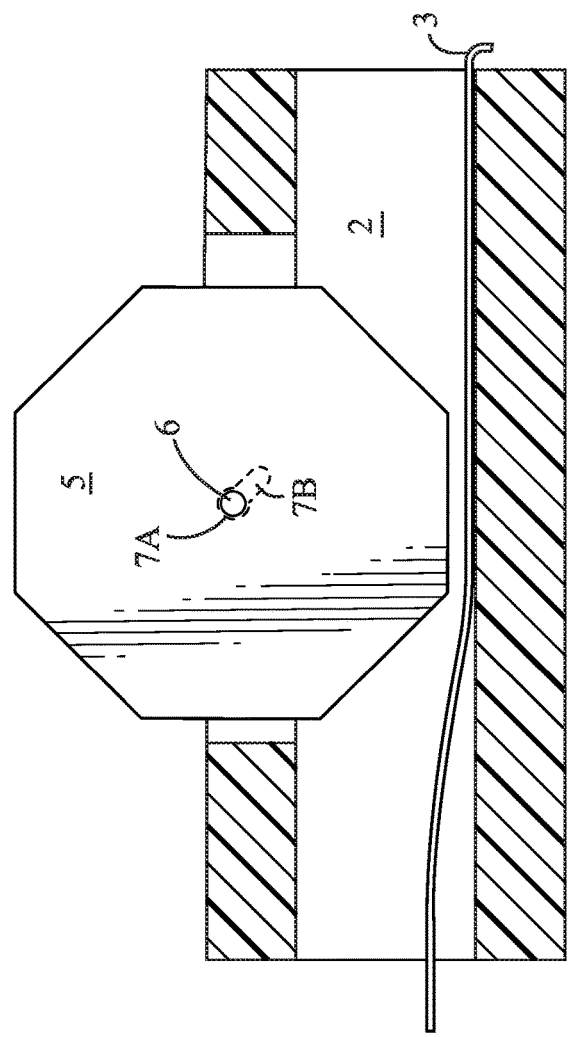
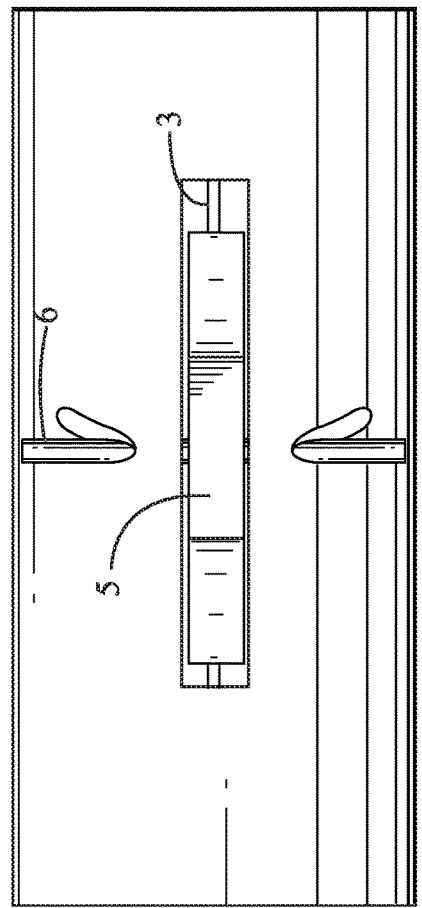
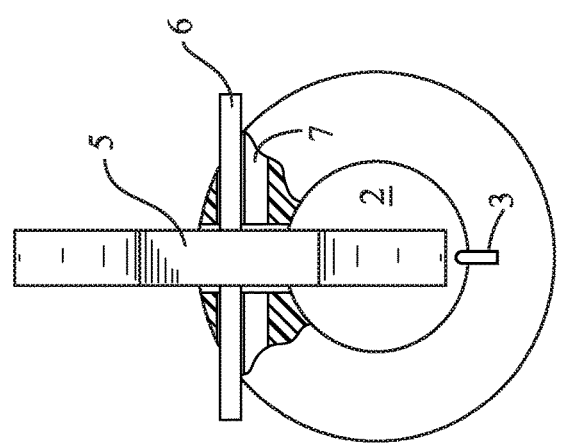
Fig. 4A
Fig. 4B
Fig. 4C

HOUSING FOR STORAGE AND MANIPULATION OF A SURGICAL GUIDE WIRE

CROSS REFERENCE TO RELATED APPLICATIONS

This application is based on U.S. Provisional Application No. 62/866,165, filed on 25 Jun. 2019, which is hereby incorporated by reference in its entirety.

SUMMARY

A housing has a spiral passageway holding a catheter which may be manually extracted from the housing by means of a wheel having a polygonal or otherwise textured circumferential surface and mounted on a shaft which extends through a non-circular bearing defined in an outer portion of the housing. An inner portion of the wheel extends into the spiral passageway adjacent the wire catheter and an outer portion of the wheel extends outwardly from the housing, whereby the upper surface of the wheel can be manipulated by a member of the surgical team in one direction and the wire catheter below the knob will be advanced in the opposite direction. When the shaft is moved into a sloping portion of the non-circular bearing, the operator can push the wheel in one direction to force it against the wire catheter and lock the catheter into intimate contact with a lower surface of the passageway, and in the opposite direction to retract the wheel slightly away from the catheter thereby permitting limited movement of the catheter relative to the housing.

DRAWINGS

Figure 2:
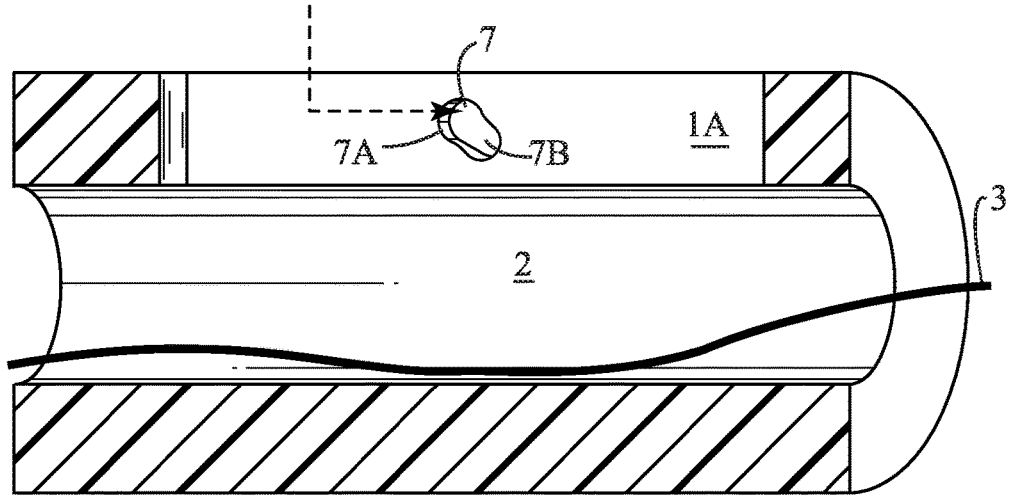
FIG. 2 is an exploded view of the wheel and a portion of the housing of FIG. 1, showing the axle about which the wheel rotates, a non-circular bearing in the sides of the housing for supporting the axle, and a portion of the passageway holding the catheter.
Figure 3A:
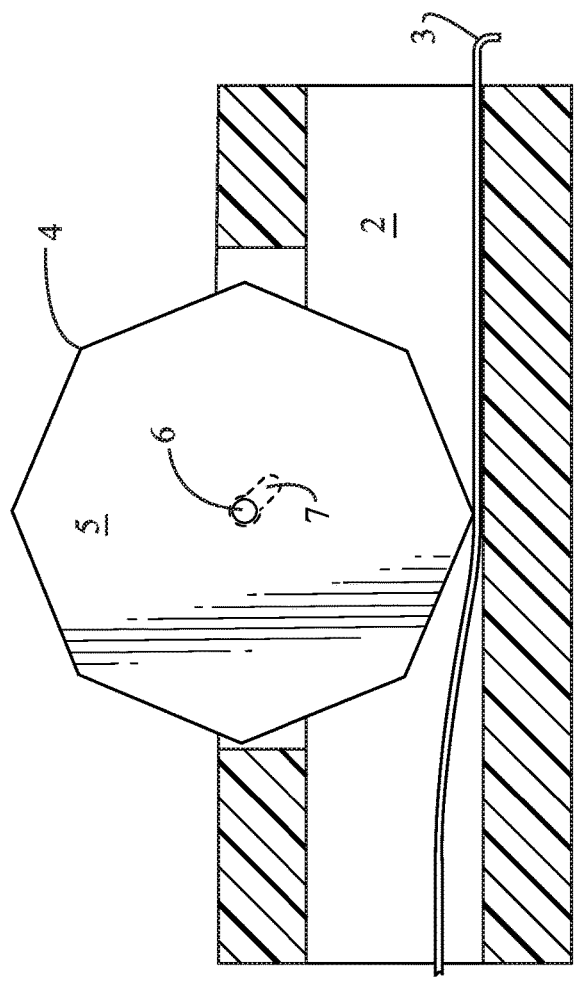
Figure 3B:
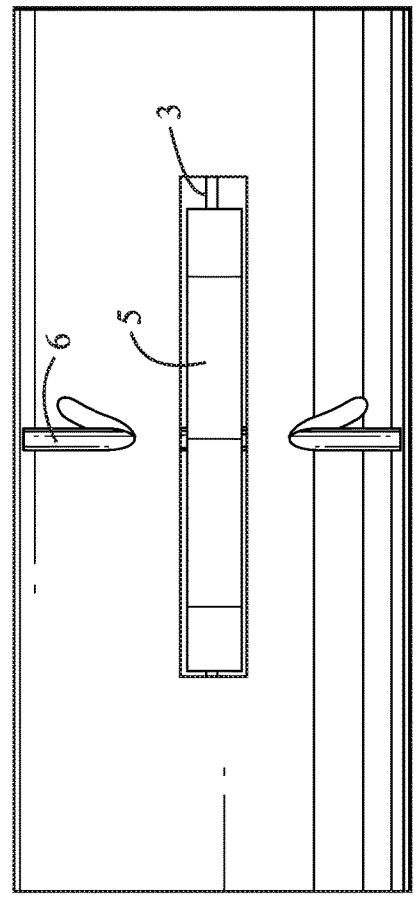
Figure 3C:
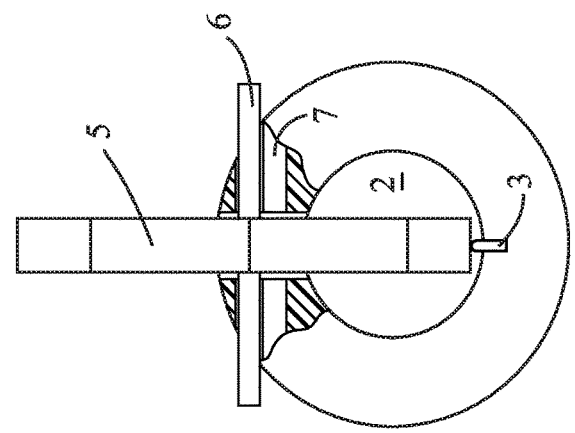

FIG. 3 comprising FIGS. 3A, 3B and 3C, are respective front, side and top views of the corresponding portion of the assembled housing and wheel of FIG. 2, in which the axle is supported in the circular upper portion of the bearing, with an apex of the wheel in contact with the catheter.

FIG. 4 is similar to FIG. 3, but with a flat surface of the wheel spaced above the catheter.

FIG. 5 is similar to FIGS. 3 and 4, but with the axle of the wheel supported in the downwardly extending portion of the bearing, with a flat surface of the wheel pressing against the catheter.

DETAILED DESCRIPTION OF AN EXEMPLARY EMBODIMENT

Figure 1:
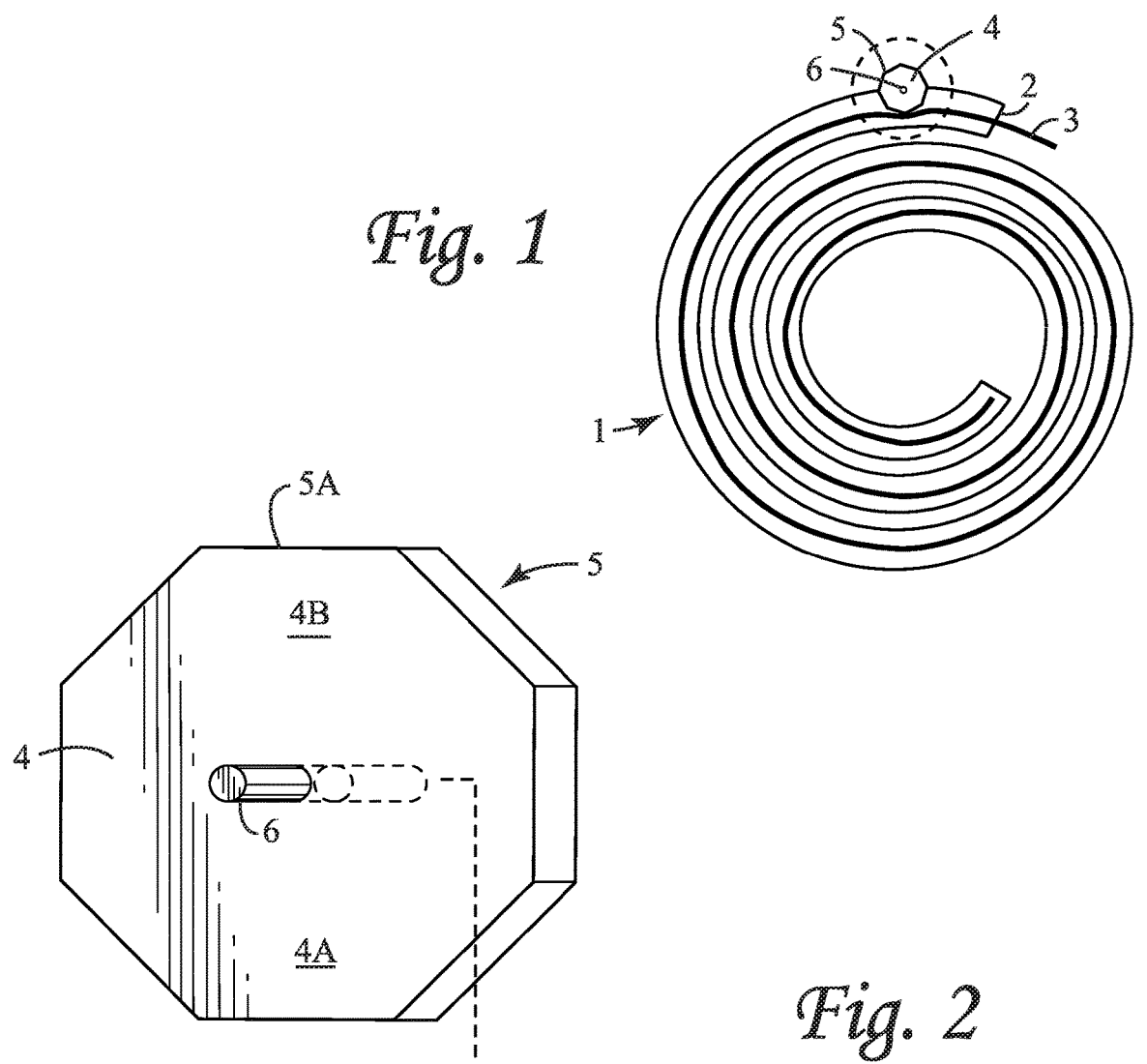
FIG. 1 is a conceptual sketch showing a spiral housing containing a catheter, with the textured circumference of a wheel in contact with the catheter and with a portion of the wheel extending into the spiral housing and into contact with the catheter.

FIG. 1 shows a housing 1 having a spiral passageway 2 containing a wire catheter 3 which may be manually extracted from the housing by means of a wheel shaped knob 4 having a textured or polygonal circumferential surface 5 (represented in the Drawings as an 8-sided polygon). The knob is mounted coaxially on a shaft 6 which extends through a non-circular bearing 7 defined in an outer portion of the housing 8 with a lower portion 4A of the knob 4 extending into the spiral passageway 2 adjacent the wire catheter 3 and an outer (upper) portion 4B of the knob 4 extending outwardly from the housing 1 whereby the upper surface 5A of knob 4B can be manipulated by a member of the surgical team in one direction and the wire catheter 3 below the knob will be advanced in the opposite direction.

FIG. 2 is a more detailed exploded view of the knob 4 and its shaft 6, and the corresponding portion of the non-circular bearing 7 in an outer portion 1A of the housing 1 above the spiral passageway 2 containing the wire catheter 3. In particular, it will be noted that the non-circular bearing 7 has a generally circular outer portion 7A in which the textured surface of the knob 4 is only intermittently in contact with the catheter 3 whereby the wire catheter may be advanced, and a generally linear inner portion 7B sloping inwardly towards the wire catheter 3 for maintaining the textured outer surface 5 of the knob in close contact with the wire catheter 3 whereby the catheter is constrained between the opposing surfaces of the knob 4 and the spiral passageway 2.

As best seen in FIGS. 3A, 3B, and 3C and in FIGS. 4A, 4B, and 4C, when the knob's shaft 6 is held loosely in the circular outer bearing portion 7A, the wire catheter 3 is free to travel. In particular, as shown in FIGS. 3A, 3B, and 3C, when the relatively rough (e.g., high friction) surface of the knob 4 is pressing against the catheter, the relatively smooth lower surface of the spiral passageway will not oppose any motion of catheter resulting from rotation of knob 4, but rather catheter 3 will be advanced incrementally into or out of the spiral passageway.

Figure 5B:
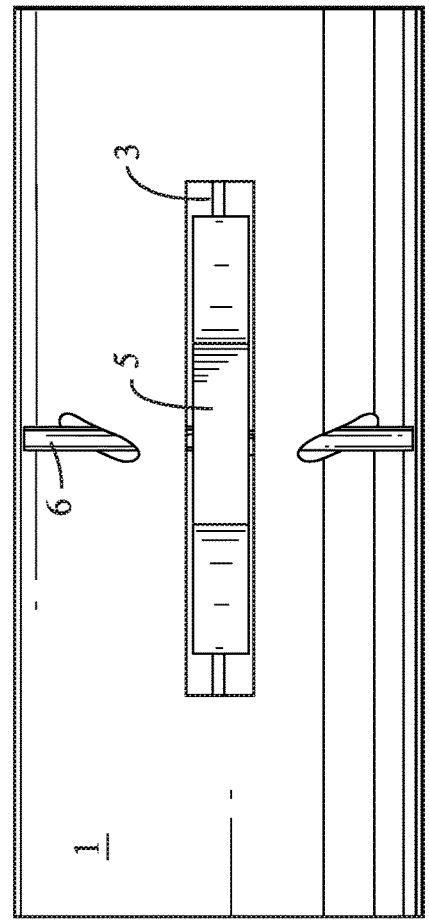
Figure 5A:
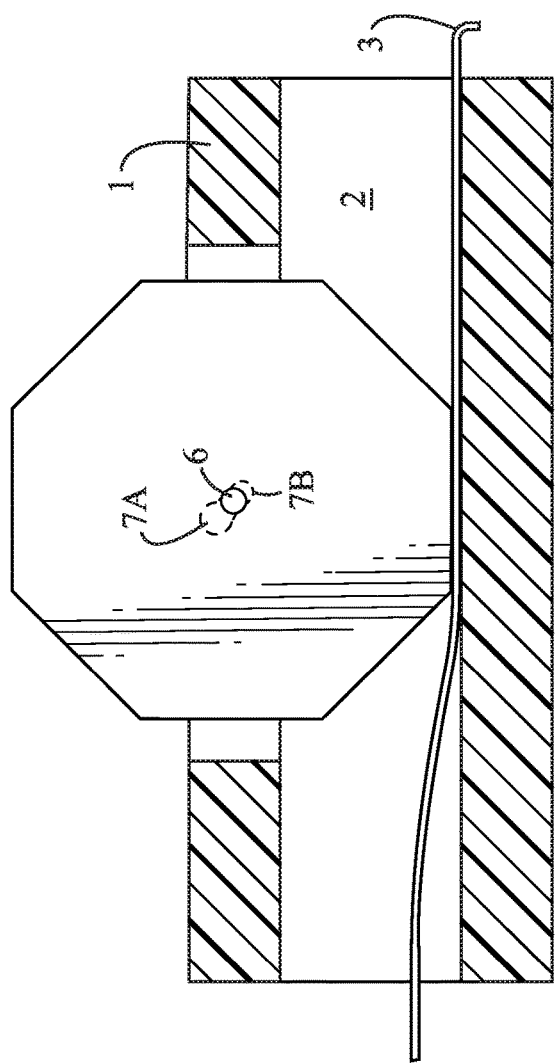
Figure 5C:
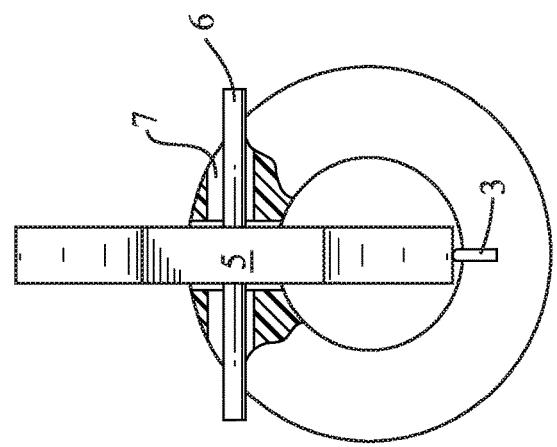

However, as best seen in FIGS. 5A, 5B, and 5C, when the knob's shaft 6 is moved into the sloping portion 7B of the bearing, the operator can push the knob 4 in one direction to force the knob against the wire catheter 3 and lock the catheter into intimate contact with the lower surface of the passageway 2, and in the opposite direction to retract the knob 4 slightly away from the catheter, thereby permitting controlled movement of the catheter relative to the housing.

The invention claimed is:

1. A mechanism for manipulation of a surgical guide wire, comprising:
    a hand held housing including an outer portion forming a spiral passageway for containing the guide wire;
    a non-circular bearing defined in the outer portion of the spiral passageway;
    a disk shaped knob having a textured circumference about an axis of rotation, the textured circumference having a textured surface, the textured surface including an inner portion and an outer portion, the inner portion of the textured circumference extending into the spiral passageway and into contact with the guide wire and an outer portion of the textured circumference extending out of the hand held housing for facilitating manual rotation of the disk shaped knob relative to the hand held housing; and
    an axial shaft extending along the axis of rotation of the disk shaped knob and confined within the non-circular bearing of the spiral passageway for limiting radial movement of the axial shaft relative to the hand held housing and for securing the disk shaped knob to the outer portion
    the non-circular bearing having an inner surface portion extending towards the guide wire for allowing the textured circumference of the disk shaped knob to be pressed inwardly against an outer surface of the guide wire and thereby force an inner surface of the guide wire into intimate contact with an adjacent inner surface of the spiral passageway whereby the guide wire is immobilized relative to the hand held housing, and an outer bearing surface further from the guide wire than the inner surface portion for allowing the disk shaped knob to rotate freely relative to the guide wire and the guide wire to move freely relative to the hand held housing when the axial shaft is in contact with the outer surface of the non-circular bearing; and the inner surface portion and the outer bearing surface of the non-circular bearing being displaced longitudinally and radially relative to the adjacent inner surface of the spiral passageway, whereby when an operator presses the disk shaped knob firmly in a first direction relative to the adjacent inner surface of the spiral passageway, the disk shaped knob is forced downwardly towards the guide wire whereby the guide wire is locked relative to the hand held housing, and when the disk shaped knob is allowed to move in a second direction opposite from the first direction, the pressure between the guide wire and the spiral passageway is reduced, while still permitting sufficient pressure between the disk shaped knob and the guide wire to control movement of the guide wire relative to the hand held housing such that the guide wire is operable to be advanced incrementally into and out of the spiral passageway by rotation of the disk shaped knob.

2. The mechanism of claim 1 wherein the effective coefficient of friction between the textured surface of the disk shaped knob and the guide wire is greater than the coefficient of friction between the guide wire and the spiral passageway.

3. The mechanism of claim 2 wherein a longitudinal portion of the non-circular bearing is oriented at an angle relative to the spiral passageway such that when the disk shaped knob is rotated in a first direction corresponding to retraction of the guide wire into the hand held housing, the textured surface of the disk shaped knob moves deeper into the spiral passageway thereby locking the guide wire relative to the spiral passageway, and when the disk shaped knob is rotated in a second direction opposite to the first direction, the guide wire is no longer forced into intimate contact with the spiral passageway and the guide wire is controllably ejected from the hand held housing.

4. The mechanism of claim 1 wherein the textured circumference is a polygonal circumference.

* * * * *